(12) United States Patent
Amtmann et al.

(10) Patent No.: US 6,881,751 B2
(45) Date of Patent: Apr. 19, 2005

(54) MEDICAMENT CONTAINING PLATINUM COMPLEX COMPOUNDS AND THE USE THEREOF

(75) Inventors: Eberhard Amtmann, Heidelberg (DE); Gerhard Schilling, Ladenburg (DE)

(73) Assignee: Ruprecht Karls Universitat (DE)

( * ) Notice: Subject to any disclaimer, the term of this patent is extended or adjusted under 35 U.S.C. 154(b) by 157 days.

(21) Appl. No.: 09/784,618

(22) Filed: Feb. 15, 2001

(65) Prior Publication Data

US 2002/0004526 A1 Jan. 10, 2002

Related U.S. Application Data

(63) Continuation of application No. PCT/DE99/02656, filed on Aug. 25, 1999.

(30) Foreign Application Priority Data

Aug. 25, 1998 (DE) .......................................... 198 38 547

(51) Int. Cl.$^7$ ............................................. A61K 31/28
(52) U.S. Cl. ...................................................... 514/492
(58) Field of Search ......................................... 514/492

(56) References Cited

U.S. PATENT DOCUMENTS

| 4,843,161 A | 6/1989 | Lippard et al. ................ 546/10 |
| 4,885,376 A | 12/1989 | Verkade ........................ 556/18 |
| 5,068,375 A | 11/1991 | Singhal ....................... 556/136 |
| 5,844,001 A | 12/1998 | McClay et al. ............. 514/648 |

FOREIGN PATENT DOCUMENTS

| EP | 0163316 | 4/1985 | ........... C07F/15/00 |
| WO | WO 94/18990 | 9/1994 | ........... A61K/33/24 |

OTHER PUBLICATIONS

CA107:108004, Osa T et al, Chemical & Pharmaceutical Bulletin, 1986, 34(9) 3563–72, abstract.*
Medline AN 90112359, Hollis L et al, J. Medicinal Chem, 1990 Jan., 33(1) 105–11, abstract.*
Medline AN 96354887, Shibusawa M et al, Cancer & Chemo., 1996 Aug., 23(9) 1149–52, abstract.*
Medline AN 1998252553, Weisman R et al, Otolaryg.–head and neck surgery, 1998 May, 118(5) 597–602, abstract.*
Medline AN 1998277308, Tessier M et al, Annales de dermatologie et de venereologie, 1996, 123 (9) 538–42, abstract.*
Fackler, J.P., et al., "Five–Coordinate Complexes of Platinum (II) and Palladium (II)", J. Am. Chem. Soc., (1968), 90(10), 2702–9.
Cornock, Margaret C., et al., "Metal Complexes of Sulphur Ligands. Part 11. Reactions of Platinum (II) and Palladium (II) Dithiocarbonates with Dithiocarbonate Ions", J. Chem. Soc., Salton Trans., (1977), (5), 496–501.

Osa, Tetsuo, et al. "Synthesis and anti tumor activity of cis–dish dichloroplatinum complexes coordinating nitrogen cyclic or sulfur compounds" Chem. Pharm. Bull. (1989), 34(9), 3563–72.

Marcheselli, L., et al., "Synthesis, characterization and evaluation of bological activity of palladium (II) and platinum (II) complexes with dithiocarbamic acids and their derivatives as ligands" Eur. J. Med. Chem. (1993), 28 (4), 347–52; and.

Sindellari, L. Et. Al, "Dithiocarbamates as antagonists of cisplatin toxicity" Inorg. Chim. Acta (1987) 137 (1–2), 109–13; and.

Mitchell, Kathryn, et al., "Isolation, Reactivity, and Molecular Structure of Pt2 u–L–SCH2 CH(COO)NHC(O)CH3–S2(bpy)2: Model of the Interaction of Platinum with Protein Sulfur Residues", Inorg. Chem. 1993, 32, 2608–2609.

Original and English Translation of: Craciunescu, D.G., et al, "Dual in vivo pharmacological activities (antitrypanosomal and antitumor) of some new complexes of platnium (II) and platinum (IV)", An. R. Acad. Farm. (1992), 58 (4), 529–49.

Kharkyevitch, D. A., (1987), *The dependence of the pharmacotherapeutic effect on the properties of pharmaceuticals and on their application conditions*. Medicine (Moscow) pp. 47–48 [English Translation of original Russian article].

* cited by examiner

*Primary Examiner*—Rebecca Cook
(74) *Attorney, Agent, or Firm*—Palmer & Dodge LLP; Kathleen M. Williams

(57) ABSTRACT

The present invention relates to a pharmaceutical preparation containing at least one compound of general formula (I)

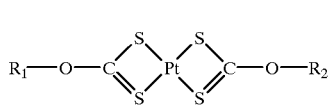

(I)

Figure 1:
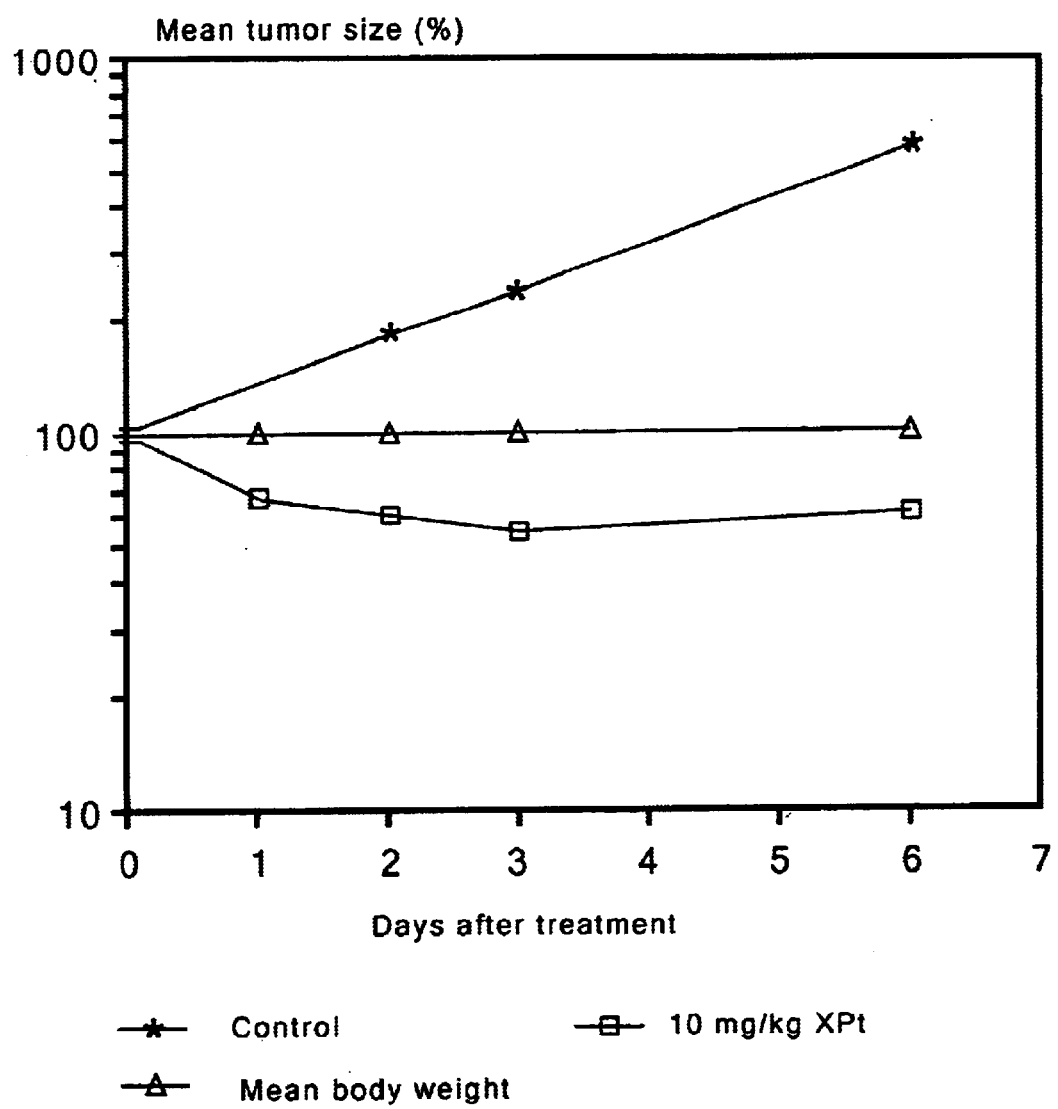

wherein $R_1$ and $R_2$ are each independently of each other a straight-chain or branched alkyl residue having 1 to 30 carbon atoms, a straight-chain or branched alkenyl residue having 2 to 30 carbon atoms, a monocyclic or polycyclic alkyl residue having 3 to 30 carbon atoms, a monocyclic or polycyclic alkenyl residue having 4 to 30 carbon atoms, or a monocyclic or polycyclic aromatic residue having 6 to 30 carbon atoms, these residues being optionally substituted by one or several substituents. This invention also relates to the use of the pharmaceutical preparations for the immunosuppressive treatment and for the non-invasive treatment.

7 Claims, 5 Drawing Sheets

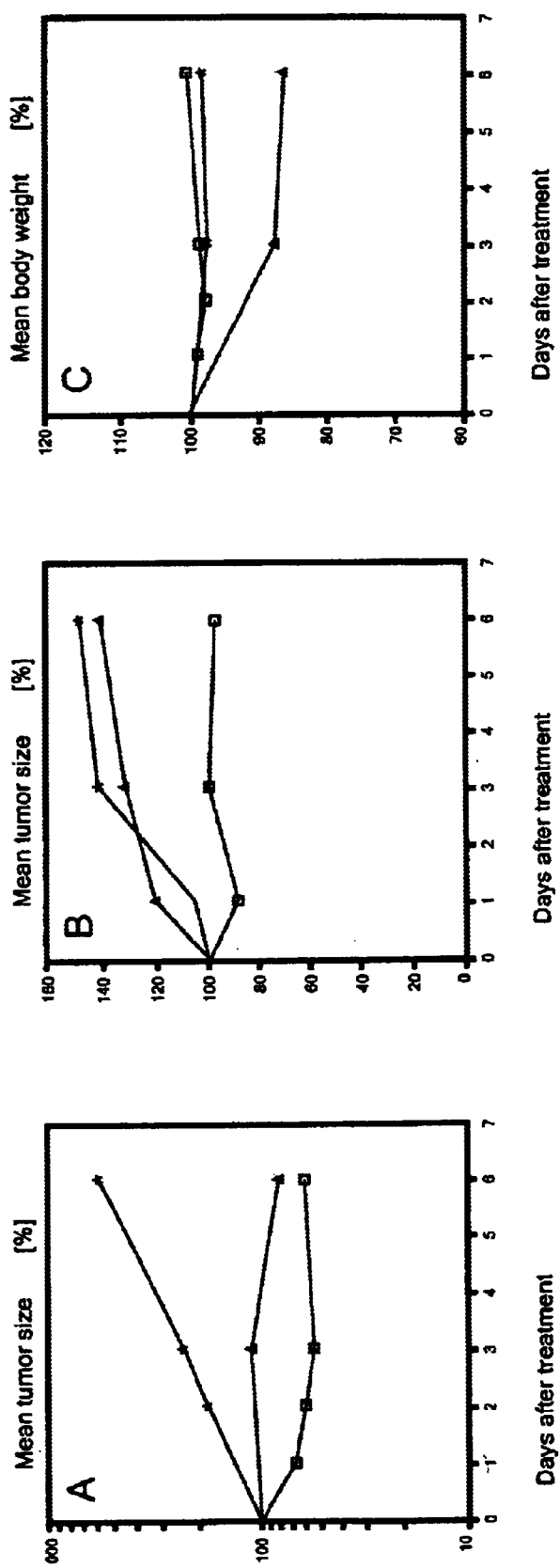

MEDICAMENT CONTAINING PLATINUM COMPLEX COMPOUNDS AND THE USE THEREOF

This application is a continuation of PCT Application No. PCT/DE99/02656, filed on Aug. 25, 1999 and published in German on Mar. 2, 2000, and of German Patent Application No. DE 1998 198 38 547.1, filed Aug. 25, 1998.

This invention relates to pharmaceutical preparations containing platinum complexes and the use thereof for treating tumoral diseases.

At present, cancerous diseases are usually treated by drug therapy or radiotherapy before and/or after an operation. Oncotherapy by drugs, i.e. chemotherapy, uses compounds influencing the cancer growth in various ways. However, chemotherapy is often accompanied by serious side-effects unpleasant for patients, such as hair loss, nausea, vomiting, tiredness, damage of bone marrow and white blood cells. This applies particularly to the platinum compounds used so far, such as cisplatin or carbo-platinum. More or less serious secondary infections also occur frequently. In addition, not all of the tumor kinds respond to chemotherapy, e.g. renal cell carcinoma or tumors of the gastro-intestinal tract.

Thus, it is the object of the present invention to provide an effective drug for treating cancerous diseases. The drug shall be effective in little dosage, have as little toxic effect on healthy cells as possible and little side-effects. Moreover, the drug shall also be suitable for local chemotherapy and be administrable by way of out-patient treatment. Besides, the drug shall also lower the risk a relapse. In addition, it shall be possible to store the drug without loss of action over a prolonged period of time.

It was found surprisingly that complexes of platinum and xanthogenate form stable compounds having an excellent anti-tumoral effect.

Therefore, the subject matter of the invention relates to pharmaceutical preparations containing platinum complexes of general formula (I)

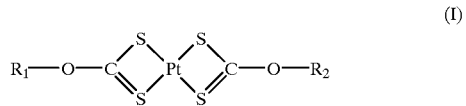

(I)

wherein $R_1$ and $R_2$ are each independently of each other a straight-chain or branched alkyl residue having 1 to 30 carbon atoms, a straight-chain or branched alkenyl residue having 2 to 30 carbon atoms, a monocyclic or polycyclic alkyl residue having 3 to 30 carbon atoms, a monocyclic or polycyclic alkenyl residue having 4 to 30 carbon atoms, or a monocyclic or polycyclic aromatic residue having 6 to 30 carbon atoms, these residues being optionally substituted by one or several substituents.

$R_1$ and $R_2$ may be the same or differ from each other.

$R_1$ and $R_2$ are preferably straight-chain $C_{1-14}$ alkyl residues or $C_{3-14}$ cycloalkyl residues. $R_1$ and $R_2$ preferably denote $CH_3CH_2$.

Any straight-chain or branched $C_{1-30}$ alkyl residue may be used. Examples thereof are methyl, ethyl, propyl, isopropyl, butyl, isobutyl, tert.-butyl, n-butyl, n-hexyl-, 2-methylpentyl-, 2,3-dimethylbutyl-, n-heptyl, 2-methylhexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl groups. Because of their better solubility short alkyl chains, such as methyl, ethyl, propyl and isopropyl groups, are preferred.

Any straight-chain or branched $C_{2-30}$ alkenyl residue can be used. Examples thereof are vinyl, propenyl, isopropenyl, allyl, 2-methylallyl, butenyl or isobutenyl, hexenyl or isohexenyl, heptenyl or isoheptenyl, octenyl, or isooctenyl groups. Vinyl, propenyl and isopropenyl groups are preferred.

The cycloalkyl residue having 3 to 30 carbon atoms may be any cycloalkyl residue. Examples thereof are cyclopropyl, cyclobutyl, cyclopentyl or cyclohexyl, cycloheptyl, cyclooctyl, cyclononyl or cyclodecyl groups. Cyclopropyl, cyclobutyl, cyclopentyl and cyclohexyl groups are preferred.

The cycloalkenyl residue having 4 to 30 carbon atoms may be any cycloalkenyl residue. Examples thereof are cyclobutenyl, cyclopentenyl or cyclohexenyl, cycloheptenyl, cyclooctenyl, cyclononenyl or cyclodecenyl groups. Cyclobutenyl, cyclopentenyl or cyclohexenyl groups are preferred.

Examples of polycyclic alkyl residues and alkenyl residues, respectively, are norbornane, adamantane or benzvalene.

$R_1$ and $R_2$ may also be any monocyclic or polycyclic C6–30 aryl residues. Examples thereof are a carbocyclic, monocyclic residue, e.g. the phenyl group, a heterocyclic, monocyclic residue, e.g. the groups thienyl, furyl, pyranyl, pyrrolyl, imidazolyl, pyrazolyl, pyridyl, pyrazinyl, pyrimidinyl, pyrazinyl, thiazolyl, oxazolyl, furazannyl, pyrrolinyl, imidazolinyl, pyrazolinyl, thiazolinyl, triazoly, tetrazolyl, and the positional isomers of the heteroatom or heteroatoms which may comprise these groups, a residue consisting of carbocyclic anellated rings, e.g. the naphthyl group or the phenanthrenyl group, a residue consisting anellated heterocyclic rings, e.g. benzofuranyl, benzothienyl, benzimidazolyl, benzothiazolyl, naphtho [2,3-b]thienyl, thianthrenyl, isobenzofuranyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalzinyl, naphthyridinyl, quinoxalinyl, quinazolinyl, cinolinyl, pteridinyl, carbazotyl, β-carbolinyl, acridinyl, phenazinyl, phenothiazinyl, phenoxazinyl, indolinyl, isoindolinyl, imidazopyridyl, imidazopyridmidinyl or also the anellated polycyclic systems consisting of heterocyclic monocycles as defined e.g. above, such as furo [2,3-b]pyrrole or thieno[2,3-b]furane, and particularly the phenyl, furyl groups, such as 2-furyl, imidazolyl, such as 2-imidazolyl, pyridyl, such as 2-pyridyl, 3-pyridyl, 4-pyridyl, pyrimidinyl, such as pyridmid-2-yl, thiazolyl, such as thiazol-2-yl, thiazolinyl, such as thiazolin-2-yl, triazolyl, such as triazolyl-2-yl, tetrazolyl, such as tetrazole-2-yl, benzimidazolyl, such as benzimidazole-2-yl, benzothiazolyl, benzothiazole-2-yl, purinyl, such as purin-7-yl or quinolyl, such as 4-quinolyl.

Preferably present substituents of the differing above-mentioned residues may be selected from the following group:

halogen: fluorine, chlorine, bromine, iodine, amino, alkylamino, dimethylamino or ethylamino, dialkylamino, such as dimethylamino, diethylamino, methylethylamino, each of these dialkylamino residues being optionally present in oxide form, amino alkyl such as aminomethyl or aminoethyl, dialkylaminoalkyl, such as dimethylaminomethyl or dimethylaminoethyl, dialkylaminoalkyloxy, such as dimethylaminoethyloxy, hydroxyl, free esterified carboxyl group, such as alkoxy carbonyl, e.g. methoxycarbonyl or ethoxycarbonyl, or converted into a salt, e.g. by a sodium or potassium atom, alkyl having 1 to 8 carbon atoms, such as methyl, ethyl, propyl, isopropyl, butyl, isobutyl, tert.-butyl, optionally substituted by one or several halogen atom(s), e.g. by fluorine, such as trifluoromethyl, oxo, cyano, nitro, formyl, acyl, such as acetyl, propionyl, butyryl, benzoyl, acyloxy, such as acetoxy or a residue of formula:

—O—CO—$(CH_2)_n CO_2 H$, wherein n=1 to 5, alkoxy, such as methoxy, ethoxy, propyloxy, isopropyloxy, butyloxy, alkylthio, such as methylthio, ethylthio, propylthio, isopropylthio, butylthio, carbamoyl, alkenyl, such as vinyl, propenyl, alkinyl, such as ethinyl, propinyl, and aryl, such as phenyl, furyl, thienyl.

An alkyl residue, substituted by one or several halogen atom(s), such as trifluoromethyl, trifluorobutyl, pentafluoropropyl, pentafluorobutyl, pentafluoropentyl, heptafluorobutyl, or nonafluorobutyl group or 2-chloroethyl can be mentioned as examples of such substituted residues.

All in all, compounds of above formula (I) can be described by the expression "thioplatin compounds".

The compounds of formula (I) are preferably produced by a process which is characterized in that a ligand exchange reaction from a platinum complex, such as e.g. cis-chlorodiammineplatinum (II), is carried out with the corresponding xanthogenate in known manner. This is e.g. a process which is characterized in that a compound of formula

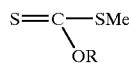

wherein Me denotes an alkali or alkaline earth metal and R has the definition indicated for $R_1$ and $R_2$, is reacted with a platinum complex such as cis-dichlorodiammineplatinum (II) and the resulting new platinum complex is isolated.

The compounds of formula (I) are suitable for treating various cancerous diseases, such as testicular tumors, ovarian carcinomas, bladder carcinomas, colonic carcinomas, prostatic carcinomas, parvocellular and non-parvocellular bronchial carcinomas, carcinomas of the cephalic and cervical parts, carcinomas of the thoracic and abdominal regions, cervical and endometrial carcinomas, sarcomas and melanomas as well as leukemias. The treatment of the parvocellular bronchial carcinoma or colorectal carcinoma is preferred. The treatment can also be carried out as a treatment associated with a radiotherapy or before and/or after an operation.

The compounds of formula (I) are well tolerable. The $L_{50}$ value is lower by a factor of 3 than that for the cis-platin known in tumor treatment. When a dosage having good antitumoral effects is used, hardly any side-effects occur. In particular, the feared nephrotoxicity known for cisplatin has not yet occurred in this way in the case of the thioplatin compounds. Another advantage of the compounds according to the invention is that they have a broad activity spectrum against the most varying tumors and are particularly also effective against tumors which have resisted treatment with platinum compounds (e.g. cisplatin) so far. Thioplatin is particularly suitable for solid tumors.

Another advantage consists in that the effectiveness of the compounds according to the invention is greater in the slightly acidic pH range than in the alkaline one, since many tumor tissues have a rather acidic environment. The inventors carried out investigations with bis[O-ethyldithiocarbonato] platinum (II), a platinum coordination complex according to formula (I) in which platinum is complexed with sulfur atoms. Following protonation, two sulfur ligate ions open reversibly (so that an aqua complex forms) which can initiate a cross-linkage of DNA. After raising the pH value, the protons dissociate from the sulfur atoms and the inert molecule is recovered. The following pH-dependent reaction equation is set up for this purpose:

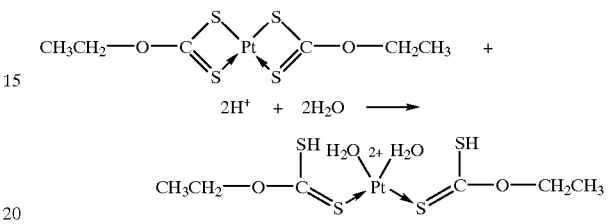

It is evident from this equation that a shift of the pH-value to the (slightly) acidic range from the prodrug according to formula (I) effects the formation of the actually reactive compound. This concept is confirmed by the examples.

The pharmaceutical preparation according to the invention can be administered in various ways, e.g. orally, parenterally, cutaneously, subcutaneously, intravenously, intramuscularly, rectally or intratuomorally. The intravenous or intratumoral administration is preferred, i.e. the administration in certain diseased organs or parts of the body. The pharmaceutical preparation is administered to a patient over a period to be determined by a physician. The pharmaceutical preparation can be administered to both human beings and mammals.

The dosage of the compound according to the invention is determined by a physician by means of the patient-specific parameters, such as age, weight, sex, severity of the disease, etc. The dosage is preferably from 0.001 to 1000 mg/kg body weight.

In accordance with the kind of administration, the pharmaceutical preparation is formulated in a suitable way, e.g. in the form of simple or coated tablets, hard or soft gelatin capsules, powders for reconstitution prior to use, granular powders, suppositories, ovules, injectables, infusion solutions, pomades, creams, gels, microspheres, implants, which are produced according to conventional galenic processes.

The compounds of formula (I) can optionally be administered together with further active substances and with excipients common in pharmaceutical compositions, e.g. depending on the preparation to be produced talcum, gum arabic, lactose, starch, magnesium stearate, cocoa butter, aqueous and nonaqueous carriers, adipoids of animal or vegetable origin, paraffin derivatives, glycols (particularly polyethylene glycol), various plasticizers, dispersants or emulsifiers, preservatives.

Additives such as sodium chloride solution, ethanol, sorbitol, glycerol, olive oil, almond oil, propylene glycol or ethylene glycol can be used for the production of liquid preparations.

Infusions or injectable solutions are preferably produced. They are preferably aqueous solutions or suspensions, it being possible to produce them prior to use, e.g. from lyophilized preparations containing the active substance as such or together with a carrier such as mannitol, lactose, glucose, albumin and the like. The ready-to-use solutions are sterilized and optionally mixed with adjuvants, e.g. preservatives, stabilizers, emulsifiers, solution aids, buffers and/or salts for controlling the osmotic pressure. Sterilization can be achieved by sterile filtration through filters having a small pore size, whereupon the composition can optionally be lyophilized. Small amounts of antibiotics can also be added so as to maintain sterility.

The provision of the pharmaceutical preparation according to the invention in a unit dosage form for administration to a mammal requiring anticancer treatment is advantageous.

The invention also relates to pharmaceutical preparations and pharmaceutical compositions, respectively, which contain a therapeutically effective amount of the active ingredient (compound of formula (I) according to the invention) together with organic or inorganic inert solid or liquid pharmaceutically compatible carriers and diluents, respectively, which are suited for the intended administration and which show no unfavorable interactions with the active ingredients.

The invention also relates to a process for the production of a pharmaceutical composition, which is characterized by mixing the compound according to formula (I) with a pharmaceutically compatible carrier.

The drugs according to the invention may include particularly the compounds described in the experimental part and more particularly the compounds in which in above formula (I) R1 and/or R2, which may be equal or differ from each other, is a methyl, ethyl, propyl or isopropyl group.

The pharmaceutical preparations and/or pharmaceutical compositions according to the invention comprise as active substance at least one active substance as defined above. Optionally further pharmaceutical active substances can be added to the composition, such as immunosuppressive agents, e.g. cyclosporine, rapamycin, 15-deoxyspergualine, OKT3, azathioprine; cytokines (e.g. TNF), interferon, etc. In addition, the composition according to the invention can additionally contain a steroid or further cytostatic agents (e.g. cisplatin, methotrexate, aminopterin, dacarbacine, nitroso urea compounds, fluorouracil, bleomycin, daunomycin, daunorubicin, doxorubicin, mithramycin, mitomycin C, etc.).

Figure 2:
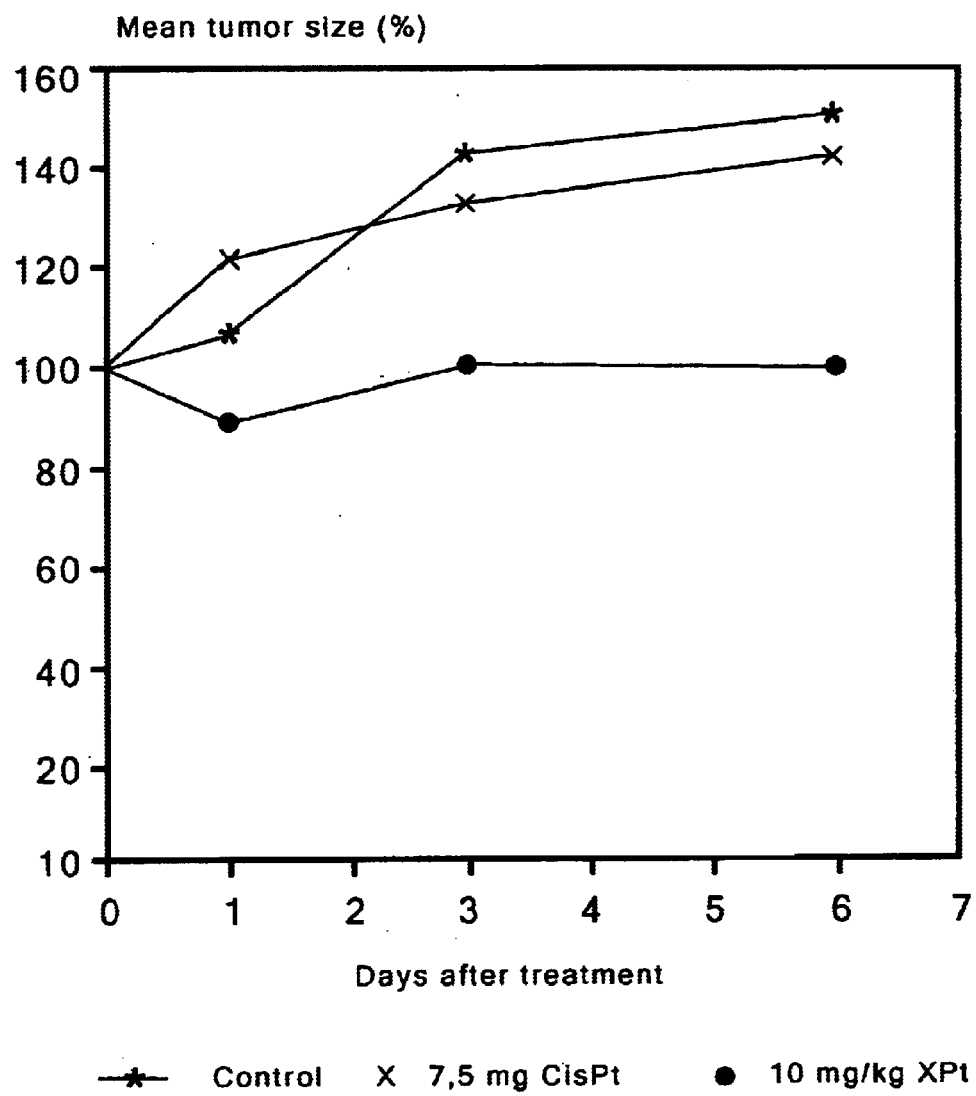
Figure 3:
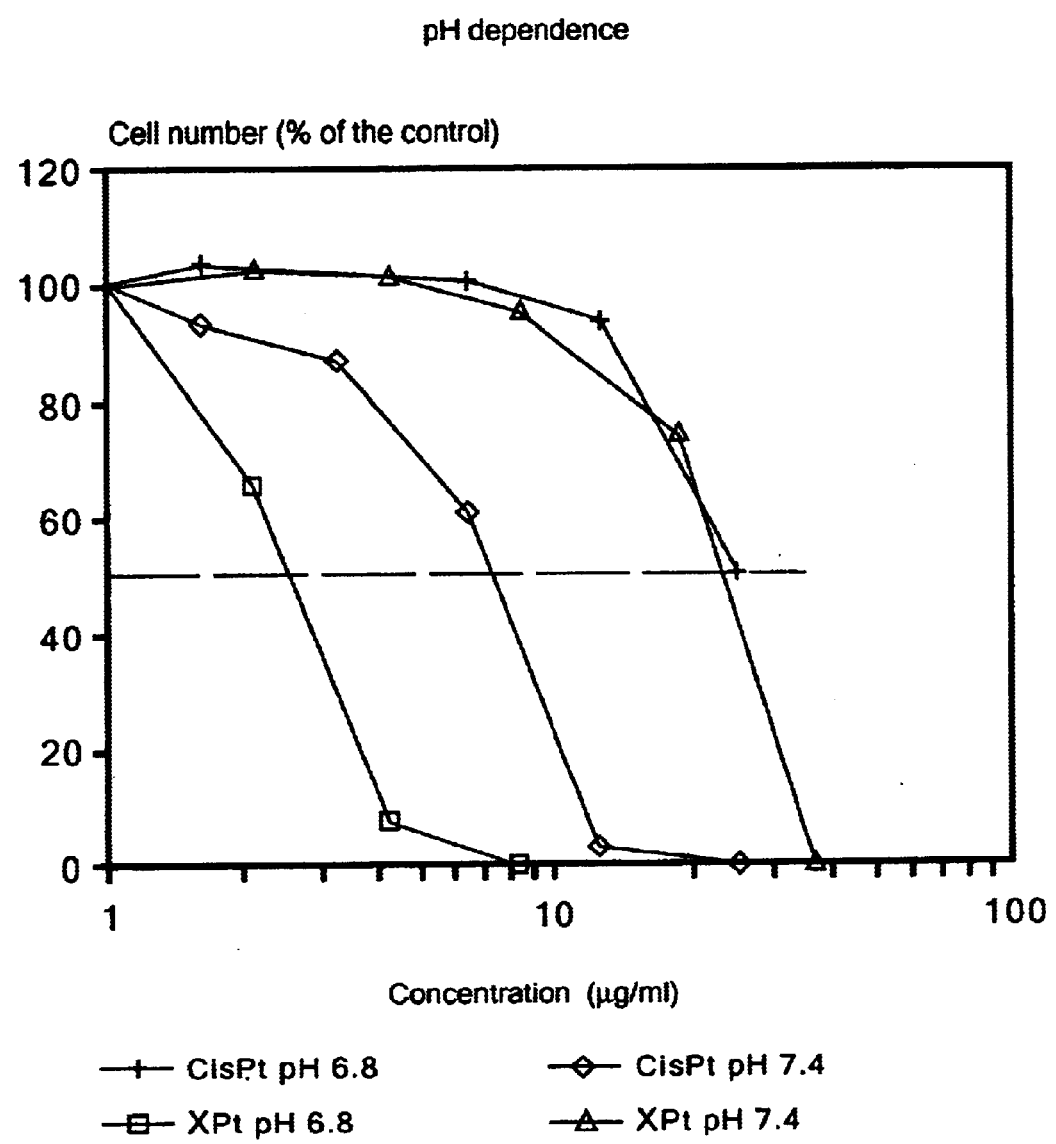
Figure 5:
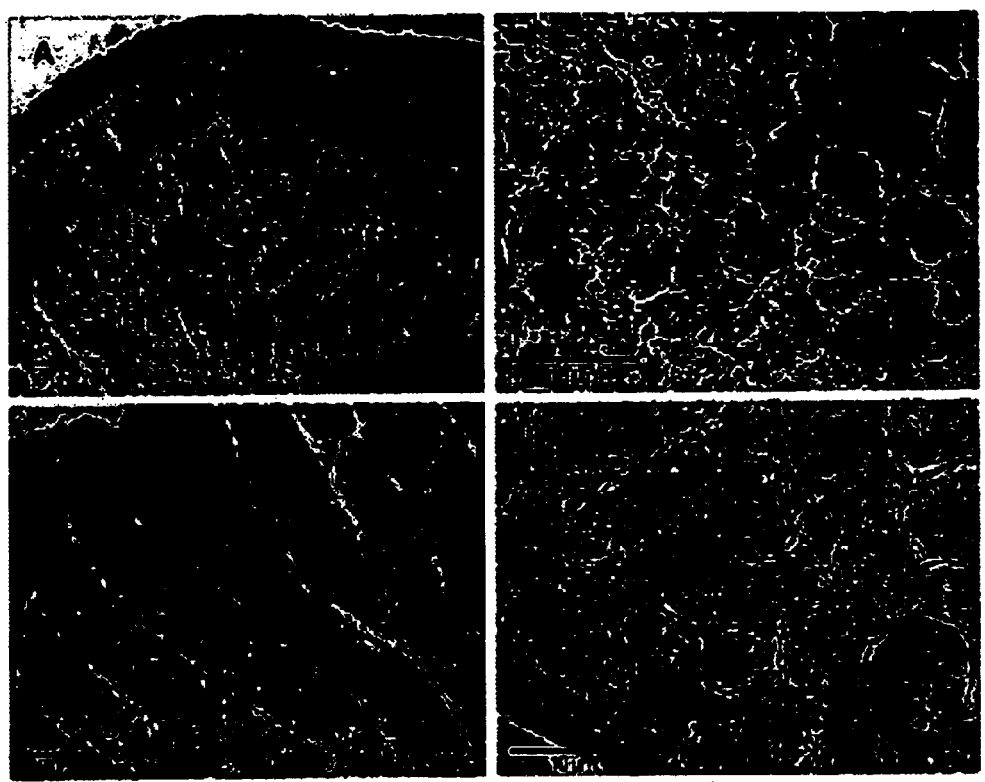
Figure 2:
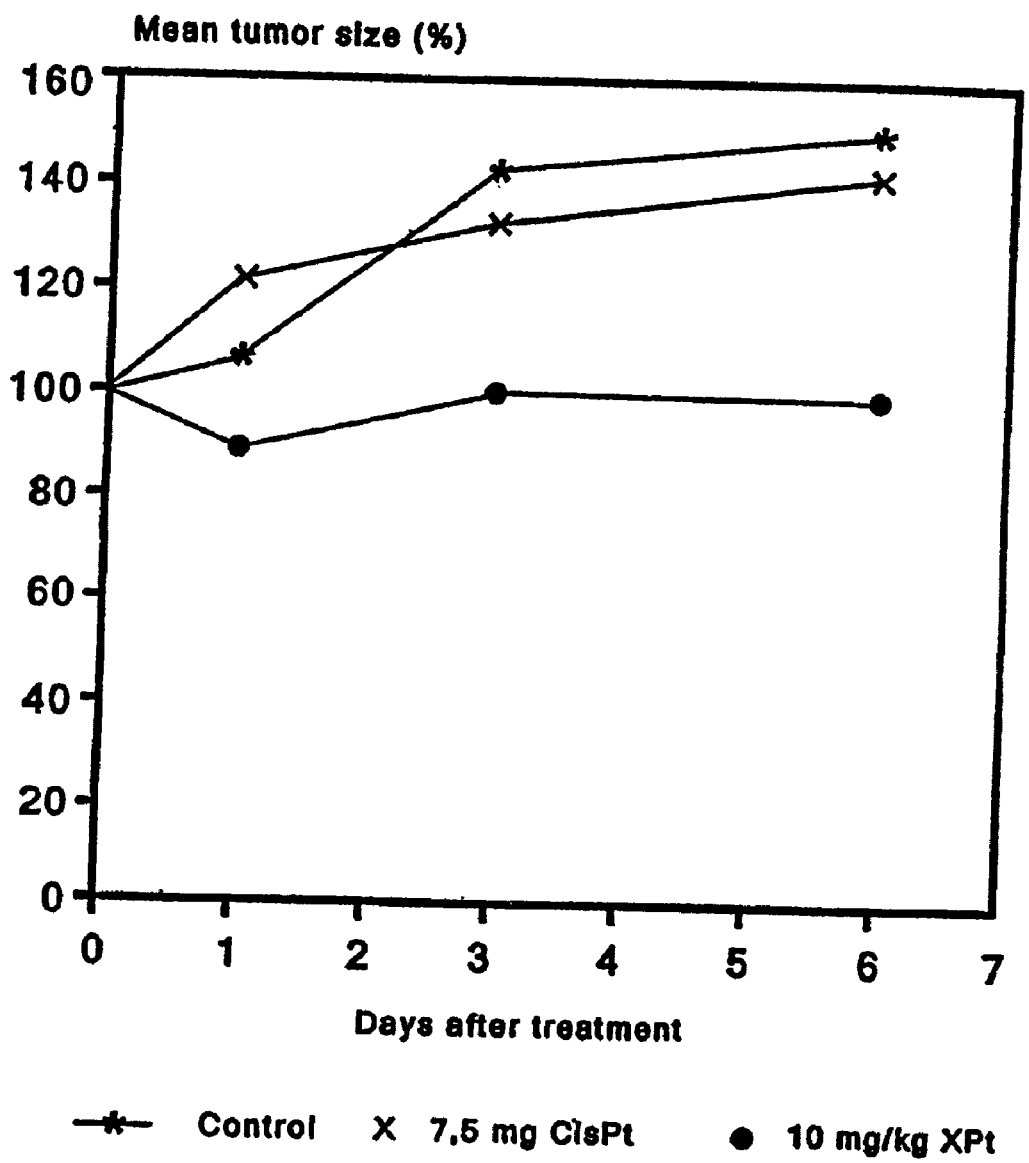
Figure 4:
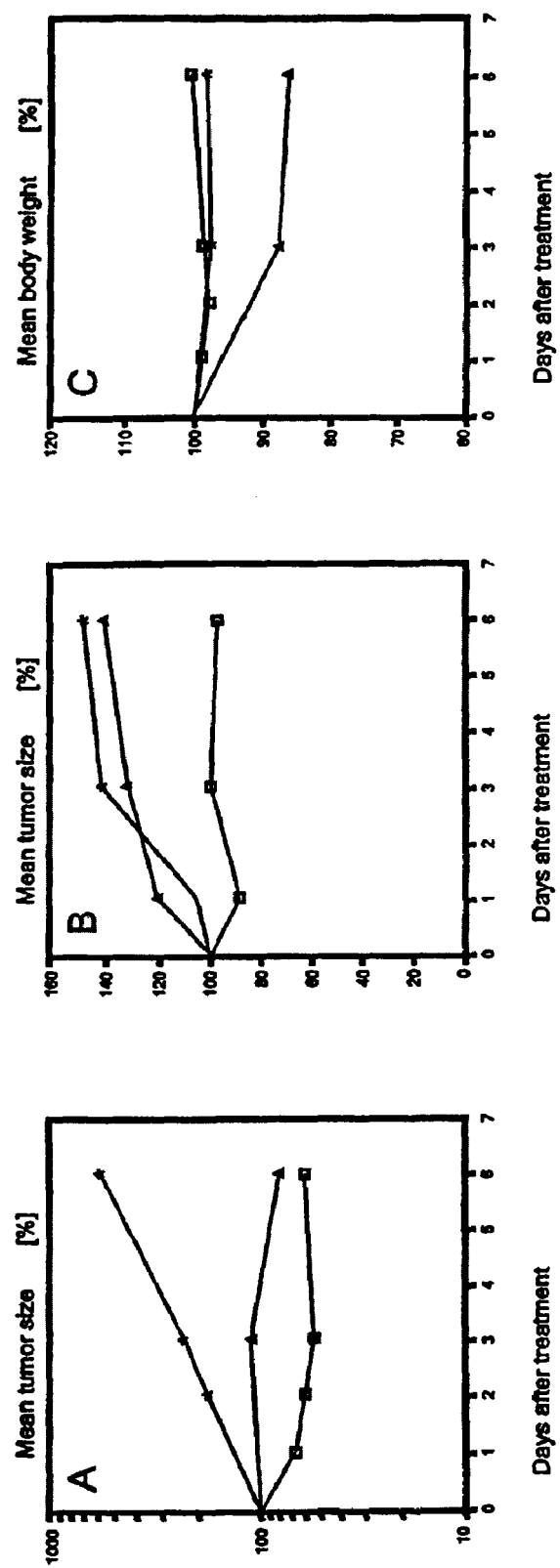

The invention is further explained by the figure:

FIG. 1 tumor regression and growth, respectively, after the treatment of a parvocellular bronchial carcinoma with a compound according to the invention and control, respectively, FIG. 2 anti-tumoral effect of a compound according to the invention on a human colon carcinoma in naked mice, FIG. 3 pH value-dependent effectiveness of cytostatic agents, FIG. 4 anti-tumoral effect of thioplatin on human xenotransplants, FIG. 5 histopathology of kidney and small intestine after treatment with thioplatin and cisplatin.

The invention is explained in more detail by the below examples.

EXAMPLE 1

A Process for the Production of diethylxanthogenateplatinum(II) Complexes (bis-[O-ethyldithiocarbanato]Platinum (II))

1 mmole cis-dichlorodiammineplatinum(II) was dissolved in 600 ml distilled water and mixed with 10 mmoles potassium ethyl xanthogenate while stirring. Stirring is carried out at room temperature for six hours. The resulting precipitate is filtered off, washed three times with distilled water and dried in vacuo. After recrystallization from warm acetone, the product is obtained as yellow crystals having a purity of over 98% in a yield of 68%.

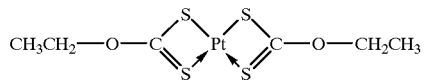

EXAMPLE 2

The following pharmaceutical composition is produced:

Injectable suspensions of the following formulation were produced:

compound of Example 1 . . . 1 g excipient (aqueous dispersion solution): benzyl alcohol, polyethylene glycol 900, carboxymethylcellulose (sodium salt), sodium chloride, water for an injectable for an ampoule of . . . 1 ml It is most preferred to add PEG up to a 5% solution thus stabilizing the solution.

EXAMPLE 3

Pharmacological Examination with the Compound According to Example 1 a) Anti-Tumoral Effect on a Human Parvocellular Bronchial Carcinoma in Naked Mice Bronchial carcinoma cells (SCLC) were implanted under the skin of six-week-old Nu/Nu mice, strain NMRI ($5 \times 10^6$ cells in 0.1 ml common salt solution). The tumors had reached a size of about 8 mm after two weeks. Then, five animals each were treated intravenously with either 0.2 ml common salt solution/0.1% BSA/1% acetone (control group) or with 10 mg/kg compound according to Example 1 in common salt solution/1% BSA/1% acetone (treated group). The tumor growth was controlled daily. The values are shown in enclosed FIG. 1.

It is clearly evident that the tumors of the mice treated with the compound according to Example 1 (treated group) decreased in size whereas tumor growth increased constantly in the mice of the control group.

b) Anti-Tumoral Effect of a Compound According to Example 1 on a Human Colon Carcinoma in Naked Mice Colon carcinoma cells (SW707) were implanted under the skin of 6-week-old Nu/Nu mice, strain NMRI ($5 \times 10^6$ cells in common salt solution). After 10 days, when the tumors had reached a size of about 10 mm, six animals each were treated with either 0.2 ml common salt solution/1% BSA/1% acetone (control group), 7.5 mg/kg compound according to Example 1 in common salt solution/1% BSA/1% acetone intravenously (treated group I) or 10 mg/kg cisplatin intravenously (treated group II). The tumor growth was controlled daily and plotted in the diagram shown in FIG. 2.

It can be inferred from FIG. 2 that the tumor growth was slowed down in treated group I whereas in the control group and treated group II a constant tumor growth could be observed. It can be seen therefrom that the compounds according to the invention are by far superior to cisplatin and display an effectiveness also in tumors which did formerly not respond to platinum compounds (cisplatin). Therefore, the compounds according to the invention have a broader activity spectrum than cytostatic agents used so far.

EXAMPLE 4 pH Dependence of the Effectiveness of Cytostatic Agents

HeLa cells were seeded in Linbro plates ($10^5$) and, after 6 hours, incubated at varying concentrations of cisplatin and a compound according to Example 1, respectively, in basal medium according to Eagle, which contained either 2.2 g (pH 7.4) or 0.85 g (pH 6.8) sodium bicarbonate and 10% fetal calf serum, at 37° C. in a 5% $CO_2$ atmosphere for 24 hours. The number of live cells was determined after vital staining using trypan blue in Neubauer's counting chamber. The result is shown in FIG. 3.

The compound according to Example 1 surprisingly has an effective maximum in the slightly acidic range, whereas the conventional cytostatic agent cisplatin produces better effects in the alkaline range. Since tumor tissue often has a slightly acidic pH value, it is obvious that because of this property the compound according to Example 1 has a better effectiveness than conventional cytostatic agents.

EXAMPLE 5
pH Dependence of the Platinum Incorporation $10^7$ HeLa cells were plated in Petri dishes and, after 4 hours, the cells were fed with a medium which included either 2.2 g/l (pH 7.4) or 0.85 g/l (pH 6.8) $NaHCO_3$. Following adjustment to a 5% $CO_2$ atmosphere, cisplatin or thioplatin were adjusted to a final concentration of 33 μM each. 4 hours after the addition of platinum, one dish of each treatment group was washed 5 times with 50 ml cold PBS each. The cells were scraped off the dishes or plates and the Pt content was determined by the neutron activation method. Following freeze-drying, the samples and platinum standards were irradiated for this purpose with neutrons ($5 \times 10^{12}$ n cm$^{-2}$sec$^{-1}$) for 30 minutes. One week later, the γ radiation of 158.4 keV and 208.2 keV was determined and the platinum concentration was determined by means of standards. The limit of the detection was 2 ng.

16 hours after the incubation, the DNA was isolated by phenol/chloroform extraction, followed by an ethanol precipitation, using other dishes or plates. The platinum content of 100 μg each was determined by the neutron activation method as described above.

| Treatment | Platinum content total cells content (ng/10⁷ cells) | Platinum content DNA (ng/mg) |
|---|---|---|
| untreated, pH 6.8 | <1 | <10 |
| untreated, pH 7.4 | <1 | <10 |
| CisPt, pH 6.8 | 140 | 14.6 |
| CisPt, pH 7.4 | 156 | 140 |
| ThioPt, pH 6.8 | 4780 | 13870 |
| ThioPt, pH 7.4 | 3680 | 1760 |

It can be inferred from the above values that, following incubation with thioplatin with a slightly acidic pH value of 6.8 an amount of platinum was bound to DNA which was almost 8 times as high as in the case of incubation with pH 7.4. The reverse effect could be observed with cisplatin, i.e. DNA was bound to cisplatin with pH 7.4 which was 10 times as high as that bound with pH 6.8. The absorption of platinum by the cells was independent of the pH. However, when thioplatin was used, the total absorption was 30 to 100 times higher than that occurring when cisplatin was used.

EXAMPLE 6
Dependence of the Cytotoxicity on the pH Value

Cells were plated in Linbro dishes or plates and, after 4 hours, the cells were fed with a medium which included either 2.2 g/l (pH 7.4) or 0.85 g/l (pH 6.8) $NaHCO_3$. Following the adjustment to a 5% $CO_2$ atmosphere, cisplatin or thioplatin were added to concentrations between 5 and 150 μM each. The number of live cells was determined 24 hours later and the $IC_{50}$ values and $IC_{99}$ values were calculated from the dose response graphs (standard deviations below 10% in all cases)

| Cell line | Cell type | $IC_{50}$ pH 6.8/7.4 Cisplatin (M) | $IC_{99}$ pH 6.8/7.4 cisplatin (M) | $IC_{50}$ pH 6.8/7.4 thioplatin (M) | $IC_{99}$ pH 6.8/74 thioplatin (M) |
|---|---|---|---|---|---|
| HeLa | Human cervical carcinoma | 86/25 | 111/54 | 5/51 | 16.3/>55 |
| H10 | Human parvocellular pulmonary carcinoma | 72/42 | >150/90 | 5.1/15.4 | 13.2/30.8 |
| SW707 | Human colorectal carcinoma | 9.6/<4.8 | 90/38.4 | 3.7/13.2 | 7.5/26.4 |
| CV1 | Mouse kidney cancer | >150/>150 | >150/>150 | 3.9/13.2 | 13.2/106 |
| Capan2 | Human pancreatic carcinoma | 143/139 | >150/>150 | 17.3/50.6 | 40.9/99 |
| Dan-G | Human pancreatic carcinoma | 45/36 | 78/72 | 15.4/52.8 | 20.9/64.5 |
| Jurkat | Human T cell lymphoma | 52.5/54 | 120/126 | 6.8/21.1 | 13.6/132 |
| S180 | Mouse sarcoma | 63/24 | >150/114 | 16.5/63.8 | 37.5/>110 |

It is evident from the Table that the cytotoxicity was much better in almost all cell lines for thioplatin with pH 6.8 than with a pH 7.4, whereas the reverse results were obtained with cisplatin, i.e. better effectiveness with pH 7.4. In all of the cases, thioplatin had a 2 to 8 times lower $IC_{50}$ with 6.8 than with 7.4. In the case of cisplatin $IC_{50}$, was poorer with pH 6.8 than with pH 7.4 or there was no detectable pH effect.

EXAMPLE 7
Antitumoral Effect of Thioplatin on Human Xenotransplants
Reference is made to FIG. 4.

Human H10 cells of a parvocellular bronchial carcinoma (A) or SW707 cells of a colorectal carcinoma (B) were injected subcutaneously into Nu/Nu-Swiss mice and, after 12 days when the tumors had reached a diameter of B to 10 mm, 5 mice were given a single i.p injection of either 10% Tween 80 (asterisk =control), 10 mg/kg cisplatin (triangles) or 10 mg/kg thioplatin dissolved to a concentration of 1 mg/ml in 10% Tween 80 (squares). The tumor sizes were determined in two directions and the relative tumor growth was calculated. The average values are shown in FIG. 4.

(C): Average body weights of the group suffering from parvocellular pulmonary carcinoma. The standard deviations were less than 3%.

It follows from FIG. 4 that cisplatin had an effect on H10 cells while in the case of colorectal carcinoma (SW707) no effect occurred even with a dose of 10 mg/kg. Thioplatin was effective in the case of both cancer kinds with the same dose. The average tumor size of the thioplatin-treated group was less than that of the cisplatin-treated group. Using thioplatin the tumor size of the parvocellular pulmonary carcinoma was reduced to 23% of that of the control group (i.e. a reduction to about ¼ of the control) whereas with cisplatin the tumor size was only reduced to 50% as compared to the control (FIG. 4A). In the case of colorectal carcinoma, cisplatin showed no effect whereas tumor growth could be prevented by means of thioplatin (FIG. 4B).

The weight loss is a rough evaluation of the toxic side effects. Whereas the cisplatin-treated animals suffered a loss of 12% and 13% on days 3 and 6 after the treatment, no weight loss was found in the thioplatin group (FIG. 4C).

EXAMPLE 8

Analysis of the Toxicity on Kidneys and Small Intestine

Reference is made to FIG. 5.

Swiss mice were given i.p. either 15 mg/kg cisplatin (A,C) or 20 mg/kg thioplatin (B,D). Four days later, histological sections of small intestine (A,B) and kidneys (C,D) were made and stained or dyed by means of hematoxylin and eosin.

The kidney of the cisplatin-treated animals showed severe degeneration and vacuolization of the tubuli (FIG. 5C). The structure of the small intestine is largely destroyed and great infiltrates can be seen in the lamina propria (FIG. 5A). In contrast thereto, the treatment with a high dose of 10 mg/kg thioplatin leaves the structures of kidney (FIG. 5D) and small intestine (FIG. 5B) unaffected.

What is claimed is:

1. A method of treating a cancerous disease sensitive to a compound of formula (I)

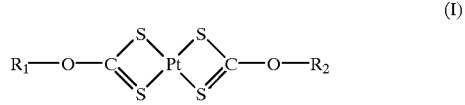

(I)

wherein $R_1$ and $R_2$ are each independently of each other a straight-chain or branched alkyl residue having 1 to 30 carbon atoms, a straight-chain or branched alkenyl residue having 2 to 30 carbon atoms, a monocyclic or polycyclic alkyl residue having 3 to 30 carbon atoms, a monocyclic or polycyclic alkenyl residue having 4 to 30 carbon atoms, or a monocyclic or polycyclic aromatic residue having 6 to 30 carbon atoms, these residues being optionally substituted by one or several substituents, comprising administering a pharmaceutical preparation comprising a pharmaceutically effective amount of at least one compound of formula (I) to a human being or a mammal in need thereof in an amount effective to treat said cancerous disease.

2. The method of claim 1, wherein said cancerous disease is parvocellular bronchial carcinoma or colorectal carcinoma.

3. The method according to claim 1, wherein said cancerous disease is selected from testicular tumor, ovarian carcinoma, bladder carcinoma, colonic carcinoma, prostatic carcinoma, parvocellular and non-parvocellular bronchial carcinoma, carcinoma of the cephalic and cervical parts, carcinoma of the thoracic and abdominal regions, cervical and endometrial carcinoma, sarcoma, melanoma and leukemia.

4. The method of claim 1, wherein in the compound of formula (I) $R_1$ and $R_2$ are each independently a straight-chain $C_{1-14}$ alkyl residue or a $C_{3-14}$ cycloalkyl residue.

5. The method of claim 1, wherein in the compound of formula (I) $R_1$ and $R_2$ are each $CH_3CH_2$.

6. The method of claim 1, wherein the compound of formula (I) is dimethylxanthogenate platinum (II) complex or dimethylxanthogenate platinum (II) complex.

7. The method of claim 1, wherein said pharmaceutical preparation further comprises a pharmaceutically compatible inert carrier or a diluent.

* * * * *

UNITED STATES PATENT AND TRADEMARK OFFICE
CERTIFICATE OF CORRECTION

PATENT NO. : 6,881,751 B2  
APPLICATION NO. : 09/784618  
DATED : April 19, 2005  
INVENTOR(S) : Amtmann et al.

Page 1 of 4

It is certified that error appears in the above-identified patent and that said Letters Patent is hereby corrected as shown below:

Title page, item "(73) Assignee: Ruprecht Karls Universitat (DE)" add the two Assignees as follows:

--(73) Assignee: Ruprecht-Karls-Universität Heidelberg (DE)  
Deutsches Krebsforschungszentrum Stiftung Des Öffentlichen Rechts (DE)--

Drawings:  
Change FIG. 2 so the reference "10" at the bottom unit on the vertifcal axis reads "0" as shown on the attached page.

Change FIG. 4 so the reference "000" at the top of the vertical axis in FIG. 4A reads "1000" as shown on the attached page.

Column 2, from line 25 through line 26, should read  
-- pyrimidinyl, pyrazinyl, thiazolyl, oxazolyl, furazannyl, pyrrolinyl, imidazolinyl, pyrazolinyl, thiazolinyl, ~~triazoly~~, triazolyl, --

Column 7, line 40, should read  
-- Treatment    Platinum content total cells    Platinum content DNA  
~~content~~ (ng/$10^7$ cells)              (ng/mg) --

Column 8, from line 7 to line 8, should read as following:

| -- Cell line | Cell type | Cisplatin ~~(M)~~ (µM) | cisplatin ~~(M)~~ (µM) | thioplatin ~~(M)~~ (µM) | thioplatin ~~(M)~~ (µM) -- |
|---|---|---|---|---|---|

UNITED STATES PATENT AND TRADEMARK OFFICE
CERTIFICATE OF CORRECTION

PATENT NO. : 6,881,751 B2
APPLICATION NO. : 09/784618
DATED : April 19, 2005
INVENTOR(S) : Amtmann et al.

It is certified that error appears in the above-identified patent and that said Letters Patent is hereby corrected as shown below:

Column 8, line 35 should read
-- than with 7.4. In the case of cisplatin $IC_{50}$[,] was poorer with --

Column 8, line 43, shoud read
-- 12 days when the tumors had reached a diameter of ~~B~~ 8 to 10 --

Signed and Sealed this

Twenty-fourth Day of October, 2006

JON W. DUDAS
*Director of the United States Patent and Trademark Office*